(12) United States Patent
Beaurline et al.

(10) Patent No.: US 6,365,166 B2
(45) Date of Patent: *Apr. 2, 2002

(54) GEL FORMULATIONS FOR TOPICAL DRUG DELIVERY

(75) Inventors: Joseph M. Beaurline, North St. Paul; Patrick J. Roddy, Mahtomedi; Mark A. Tomai, Oakdale, all of MN (US)

(73) Assignee: 3M Innovative Properties Company, St. Paul, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/325,369

(22) Filed: Jun. 4, 1999

Related U.S. Application Data

(62) Division of application No. 08/759,992, filed on Dec. 3, 1996, now Pat. No. 5,939,090.

(51) Int. Cl.[7] ............... A61K 9/00; A61K 31/4439
(52) U.S. Cl. ............... 424/400; 514/293; 514/889; 514/934; 514/944
(58) Field of Search .................. 514/944, 889, 514/934, 293; 424/434, 400

(56) References Cited

U.S. PATENT DOCUMENTS

| 4,680,312 A | 7/1987 | Johnson ............... 514/573 |
| 4,689,338 A | 8/1987 | Gerster ............... 514/293 |
| 4,788,064 A | 11/1988 | Patel et al. ............... 424/444 |
| 4,814,173 A | 3/1989 | Song et al. ............... 424/444 |
| 5,238,944 A | 8/1993 | Wick et al. ............... 514/293 |
| 5,389,640 A | 2/1995 | Gerster et al. ............... 514/293 |
| 5,492,911 A * | 2/1996 | Stief ............... 514/252 |

FOREIGN PATENT DOCUMENTS

| EP | 385630 | 9/1990 | |
| WO | 88/00587 | 1/1988 | ......... C07D/471/04 |
| WO | WO9215582 | 10/1992 | |

OTHER PUBLICATIONS

"3M's Immune Response Enhancers", Pharmoproject Magazine, Sep. 1996.

M. A. Tomai et al., "Immunomodulating and Antiviral Activities of the Imidazoquinoline S–28463", Antiviral Research, 28 (1995) 253–264.

E. Istvan et al., "The Utilization of Colloid Siliciumdioxide in the Pharmaceutical Technology", Pharmacy 19 (1975) 290–296.

* cited by examiner

*Primary Examiner*—Diana Dudash
*Assistant Examiner*—Alysia Berman
(74) *Attorney, Agent, or Firm*—MarySusan Howard; Ted K. Ringsred; Robert W. Sprague

(57) ABSTRACT

Pharmaceutical gel formulations for topical drug delivery include drug, colloidal silicon dioxide, triacetin and, preferably, propylene glycol. The gel formulations are well suited for topical delivery of the drug 4-amino-2-ethoxymethyl-α,α-dimethyl-1H-imidazo[4,5-c]quinoline-1-ethanol, which when applied topically induces cytokines, such as interferon and tumor necrosis factor, locally in the skin or mucous membranes of a mammal. The gel formulations are also well-suited for topical delivery of drugs for treatment of diseases involving skin and/or mucosal lesions because the gel formulations do not need to include irritating components.

7 Claims, 1 Drawing Sheet

GEL FORMULATIONS FOR TOPICAL DRUG DELIVERY

This is a divisional of application Ser. No. 08/759,992 Dec. 3, 1996, now U.S. Pat. No. 5,939,090.

BACKGROUND OF THE INVENTION

This invention relates to improved pharmaceutical gel formulations for the topical delivery of drugs. In another aspect, this invention relates to pharmaceutical topical gel formulations containing 4-amino-2-ethoxymethyl-α,α-dimethyl-1H-imidazo[4,5-c]quinoline-1-ethanol.

Pharmaceutical gel and cream formulations for topical delivery of drugs are well known. However, many such formulations are not suitable for certain applications due to problems with, for example, insolubility and/or degradation of the drug in the formulation, physical instability of the formulation (separation of components, thickening, precipitation/agglomerization of active ingredient, and the like), and due to irritation of the skin or mucosa to which the formulation is applied. Also, depending on the purpose of the formulation, it may be desirable if the formulation avoids systemic delivery of the active ingredient, particularly where side effects may result from such systemic delivery.

U.S. Pat. No. 5,238,944 discloses a topical formulation of 1-isobutyl-1H-imidazo[4,5-c]quinolin-4-amine which is effective for the treatment of genital warts and other diseases. However, although useful for its intended purpose, this formulation is a cream, subject to potential separation problems, and includes isostearic acid which makes it painful if applied to open lesions such as occur in the case of herpes simplex virus infection.

The compound 4-amino-2-ethoxymethyl-α,α-dimethyl-1H-imidazo[4,5-c]quinoline-1-ethanol disclosed in U.S. Pat. No. 5,389,640 is from the same chemical class of compounds as 1-isobutyl-1H-imidazo[4,5-c]quinolin4-amine, although having some significantly different chemical, physical, and biological properties. The compound has been shown to induce interferon and tumor necrosis factor in mice and rats following oral administration. The compound has also been shown to induce interferon-α, tumor necrosis factor, interleukin-1α, interleukin-1β, interleukin-6 and interleukin-8 in cultures of human peripheral blood mononuclear cells. The compound has also shown antiviral activity against herpes simplex virus-challenged guinea pigs when administered subcutaneously, dermally or intravaginally 24 hours before infection.

However, systemic administration of 4-amino-2-ethoxymethyl-α,α-dimethyl-1H-imidazo[4,5-c]quinoline-1-ethanol may also be associated with certain side effects, including fever, malaise, headache, nausea and vomiting. Non-systemic topical cytokine induction would thus have the advantage of avoiding the side effects associated with the systemic induction of these ctyokines.

SUMMARY OF THE INVENTION

Accordingly, it is one object of the present to provide a highly stable pharmaceutical gel formulation that is suitable for topical application to the skin and/or mucosa.

A related object is to provide a gel formulation that is suitable for application to skin and/or mucosal lesions.

Another object is to provide a gel formulation in which 4-amino-2-ethoxymethyl-α,α-dimethyl-1H-imidazo[4,5-c] quinoline-1-ethanol is soluble and does not substantially degrade during storage.

Yet another object is to provide a topical gel formulation for the topical delivery of 4-amino-2-ethoxymethyl-α,α-dimethyl-1H-imidazo[4,5-c]quinoline-1-ethanol which does not deliver undue amounts of the active compound systemically.

These objects, as well as others that will become apparent upon reference to the following description, are provided by pharmaceutical gel formulations including a drug, colloidal silicon dioxide, triacetin and, preferably, propylene glycol. The drug is preferably 4-amino-2-ethoxymethyl-α,α-dimethyl-1H-imidazo[4,5-c]quinoline-1-ethanol, which has been found to be sufficiently soluble and chemically stable in gel formulations of the present invention. Moreover, it has been found that gel formulations of the present invention, unlike certain other gel formulations, provide excellent topical delivery of the drug while substantially avoiding unwanted systemic delivery (thereby avoiding side effects).

As noted, the gel formulations of the invention preferably include propylene glycol. One reason is because it appears, surprisingly, that inclusion of propylene glycol thickens the gel formulations and that the integrity of the resulting gel is maintained at body temperature. It should be noted, however, that gel formulations without propylene glycol, but including 4-amino-2-ethoxymethyl-α,α-dimethyl-1H-imidazo[4,5-c]quinoline-1-ethanol, colloidal silicon dioxide, and triacetin have been found to be suitable, although less preferred.

The present invention also provides a method of inducing cytokines, such as interferon and tumor necrosis factor, locally in the skin or mucous membranes of a mammal, comprising placing on the skin or mucous membranes of a mammal an amount of a formulation as described above effective to induce cytokines. The formulations of the present invention are also well-suited for treatment of diseases by application of the formulation to skin and/or mucosal lesions because the gel formulations do not need to include irritating components.

BRIEF DESCRIPTION OF THE DRAWINGS

The invention will be described below with reference to tests conducted using apparatus shown in the accompanying drawings, wherein.

DETAILED DESCRIPTION OF PREFERRED EMBODIMENTS

Figure 1:
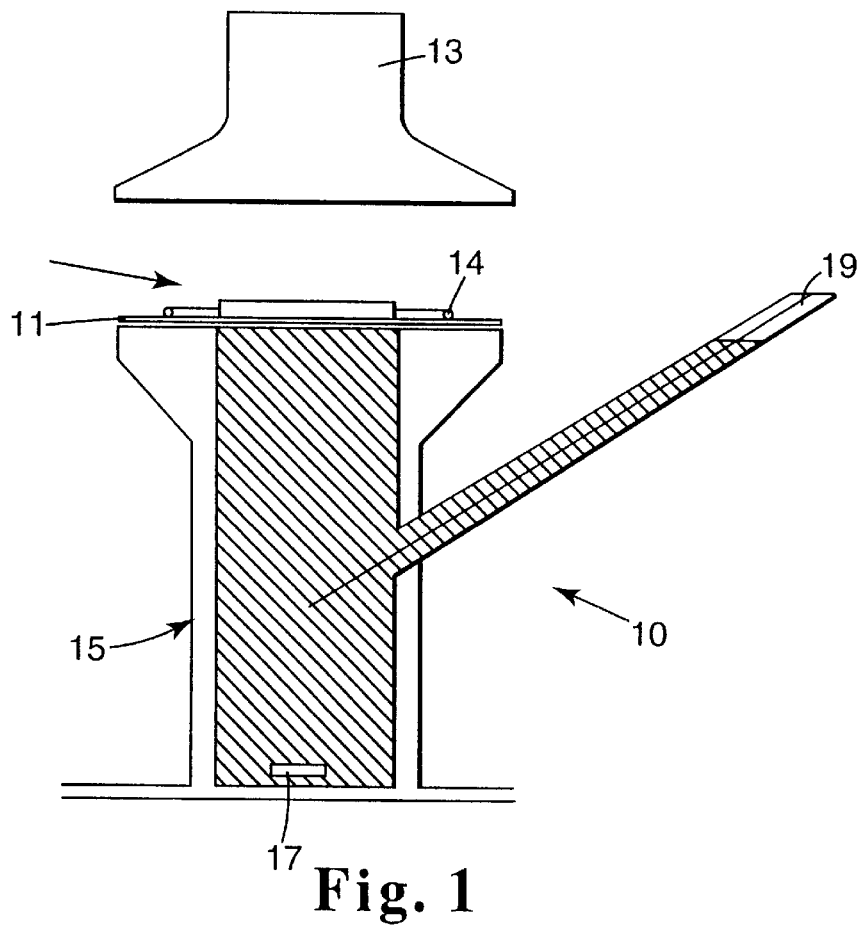
FIG. 1 is a modified Franz diffusion cell drug release test apparatus.

All weight percentages recited herein are based on the total weight of the formulation unless otherwise indicated.

The present invention provides gel formulations preferably containing 4-amino-2-ethoxymethyl-α,α-dimethyl-1H-imidazo[4,5-c]quinoline-1-ethanol (sometimes referred to herein as "the drug").

The compound 4-amino-2-ethoxymethyl-α,α-dimethyl-1H-imidazo[4,5-c]quinoline-1-ethanol is a known immune response enhancer with antiviral properties. It can be synthesized using the method disclosed in U.S. Pat. No. 5,389,640, the disclosure of which is incorporated herein by reference. The compound can be used to treat viral infections such as Type I or Type II Herpes simplex viral infections and genital warts. Furthermore, the fact that the compound induces a variety of cytokines including interferon suggests that it and topical formulations containing it may be useful in the treatment of other diseases where interferon has been shown to be effective. The 4-amino-2-ethoxymethyl-α,α-dimethyl-1H-imidazo[4,5-c]quinoline-1-ethanol will preferably be present in a formulation of the invention in a therapeutically effective amount i.e., an amount effective to treat the targeted disease state or to prevent the recurrence of such a disease. Generally 4-amino-2-ethoxymethyl-α,α-dimethyl-1H-imidazo[4,5-c]quinoline-1-ethanol will preferably be present in a formulation of the invention in an amount of 0.001 to about 0.6 percent by weight, more preferably about 0.01 to about 0.5 percent by weight based on the total weight of the formulation.

4-Amino-2-ethoxymethyl-α,α-dimethyl-1H-imidazo[4,5-c]quinoline-1-ethanol exhibits substantial solubility in formulations of the invention. Accordingly in a preferred embodiment of the invention the drug is substantially fully dissolved in the formulation.

Formulations of the invention contain colloidal silicon dioxide as a gelling agent. Colloidal silicon dioxide is commercially available under several trade names: AEROSIL from Degussa (Deutsche Gold- und Silber-Schneideanstalt vormals Roessler, Frankfurt, Germany), CAB-O-SIL from Cabot Corporation (Tuscola, Ill., USA), and Wacker HDK from Wacker-Chemie GmbH (Munich, Germany). Several grades of colloidal silicon dioxide having different surface areas are commercially available. A preferred grade has a specific surface area of about 200 $m^2/g$ and is available under the trade designation AEROSIL 200. Colloidal silicon dioxide will generally be present in a formulation of the invention in an amount of about 7 to about 12 percent, preferably about 8 to about 11 percent by weight based on the total weight of the formulation.

Formulations of the invention preferably contain propylene glycol (1,2-propanediol). The addition of propylene glycol has been found, surprisingly, to thicken the gel formulations and to provide a gel that maintains its integrity at body temperature. It is believed that the propylene glycol may act as a solvent for the colloidal silicon dioxide and as a solubilizer for the drug. Generally propylene glycol will preferably be present in a formulation of the invention in an amount of about 1 to about 30 percent, and more preferably about 5 to about 25 percent by weight based on the total weight of the formulation.

Formulations of the invention also contain triacetin (1,2,3-propanetriol triacetate). The triacetin is believed to act as a solvent for the colloidal silicon dioxide and as a solubilizer for the drug. In those formulations of the invention that do not contain propylene glycol, triacetin will generally be present in amount of about 88 to about 93 percent by weight based on the total weight of the formulation. In those formulations of the invention that do contain propylene glycol, triacetin will generally be present in an amount of about 58 to about 92 percent, preferably about 63 to about 88 percent by weight based on the total weight of the formulation. However, the actual percentages of the triacetin and other ingredients will depend on whether other ingredients are included in the formulation.

A formulation of the present invention can be prepared by combining the 4-amino-2-ethoxymethyl-α,α-dimethyl-1H-imidazo[4,5-c]quinoline-1-ethanol with the triacetin and propylene glycol, if present, and then heating with mixing to a temperature of about 50–55° C. When the 4-amino-2-ethoxymethyl-α,α-dimethyl-1H-imidazo[4,5-c]quinoline-1-ethanol appears to be completely dissolved, the colloidal silicon dioxide is added and mixed until wetted. The resulting mixture is sheared on a high speed propeller mixer until a homogeneous gel is formed.

Formulations of the invention have been found to induce interferon and tumor necrosis factor locally in the skin of mice. Local induction helps avoid the side effects associated with the systemic induction of these cytokines. As previously mentioned, these side effects include fever, malaise, headache, nausea and vomiting. The ability of the formulations of the invention to induce interferon and tumor necrosis factor in the skin suggests that they will be useful for the topical treatment of diseases such as Type I and Type II Herpes simplex infections, warts including genital warts, basal cell carcinoma, cervical intraepithelial neoplasia and actinic keratosis.

The examples set forth below are intended to illustrate the invention.

Cytokine Induction Test Method

The cytokine induction data given in the examples below were obtained using the following test method.

For each formulation being tested, two groups of hairless SKH-1 female mice (four mice per group) are dosed. A 10 μL portion of the drug containing formulation is applied to the right flank and rubbed in for 1 minute. A 10 μL portion of placebo gel (which contains the same weight percent of silicon dioxide and propylene glycol as the test gel with the remainder being triacetin) is applied to the left flank and rubbed in for 1 minute. One hour after dosing the first group of mice is sacrificed. Two hours after dosing the second group of mice is sacrificed. The skin is washed and tissue samples (100 mg) are removed from the right flank (drug treated) and the left flank (placebo treated). Individual samples are placed in cryovials and snap frozen in liquid nitrogen. The samples are then homogenized in 1 mL of RPMI medium containing 10% fetal calf serum and centrifuged at 2000 rpm for 10 minutes. The supernatants are collected and frozen until assayed for tumor necrosis factor (TNF) and interferon (INF). TNF is assayed using a commercially available ELISA kit (Genzyme, Cambridge, Mass.) and results are expressed as pg/mL±SEM. Interferon is measured by bioassay using L929 mouse fibroblasts challenged with encephalomyocarditis virus. The details of the bioassay method have been described by G. L. Brennan and L. H. Kronenberg in "Automated Bioassay of Interferons in Micro-test Plates", Biotechniques, June/July, 78, 1983, incorporated herein by reference. Briefly stated, the method is as follows: interferon dilutions and L929 cells are incubated at 37° C. for 12 to 24 hours. The incubated cells are infected with an inoculum of encephalomyocarditis virus. The infected cells are incubated for an additional period at 37° C. before quantifying for viral cytopathic effect. The viral cytopathic effect is quantified by staining followed by spectrophotometric absorbance measurements. Results are expressed as units/mL±SEM based on the value obtained for NIH mouse interferon reference standard.

Drug Release Test Method

The drug release data given in the examples below were obtained using the following test method.

A modified Franz diffusion cell 10 of the type shown in FIG. 1 is used. The cell is made of glass and holds approximately 11 mL of receptor fluid in the cell body. The cell body opening is 1.6 cm in diameter (2.0 $cm^2$ area). A section of synthetic membrane 11 (microporous polyethylene film, CoTran™ 9711 from 3M Company) is mounted between the upper portion 13 and lower portion 15 of the cell. The membrane is held in place by means of a Teflon® O-ring 14. The upper and lower portions are held together by means of a clamp (not illustrated).

The portion of the cell below the mounted membrane is completely filled with receptor fluid (0.1M sodium acetate buffer, pH 4.0) such that the receptor fluid is in contact with the membrane. The receptor fluid is stirred by means of magnetic stir bar 17 and a magnetic stirrer (not illustrated). The sampling port 19 is covered except when in use.

When a gel formulation is evaluated, the membrane is placed across the opening of the lower portion of the diffusion cell. The O-ring is positioned on top of the membrane. A 1.50 g portion of formulation is placed on top of the membrane and spread evenly over the portion of the membrane surface which lies inside the O-ring. The diffusion cell is assembled and the lower portion is filled with 11 mL of warm (32±1° C.) receptor fluid.

The sampling port is covered and the cell is placed in a constant temperature (32±1° C.) and humidity (50%±15% relative humidity) chamber. The receptor fluid is stirred throughout the experiment. The entire volume of receptor fluid is withdrawn at intervals of 30, 60, 120, 240 and 360 minutes elapsed time and immediately replaced with fresh fluid. The withdrawn fluid is analyzed for 4-amino-2-ethoxymethyl-α,α-dimethyl-1H-imidazo[4,5-c]quinoline-1-ethanol using a uv spectrophotometer equipped with a flow cell (1.0 cm for gels containing 0.05% or 0.01% drug; 0.2 cm for gels containing 0.25% drug) and measuring the absorbance at 247 nm. Results are reported as the cumulative amount of drug released at 30, 60, 120, 240 and 360 minutes and are expressed in units of mg/cm$^2$.

In Vitro Skin Penetration Test Method

The skin penetration data given in the examples below was obtained using the following test method.

Figure 2:
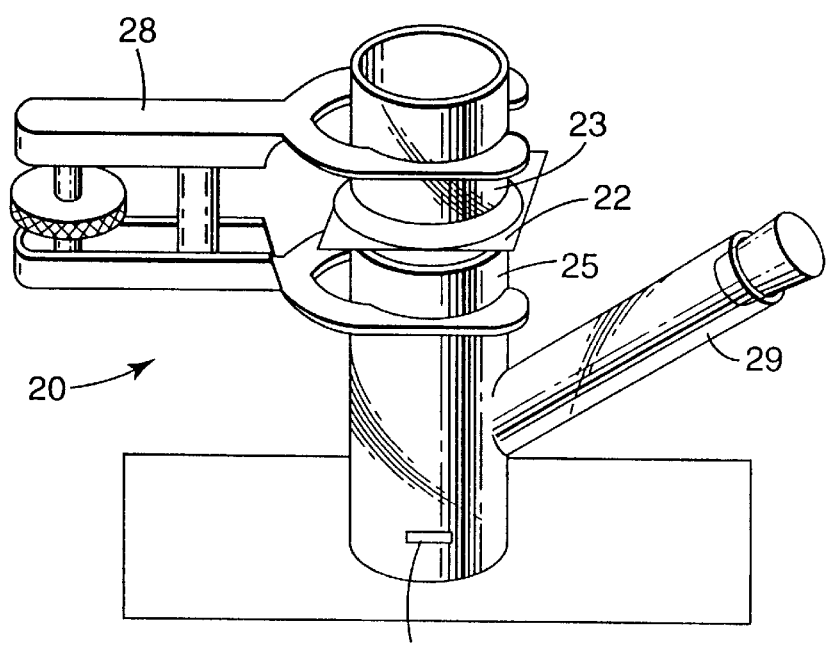
FIG. 2 is an alternative modified Franz diffusion cell drug release test apparatus.

A modified Franz diffusion cell 20 of the type shown in FIG. 2 is used. Two types of skin are used, hairless mouse skin and human cadaver skin. As shown in FIG. 2, the skin 22 is mounted between the upper portion 23 and the lower portion 25 of the cell, which are held together by means of a clamp 28.

The portion of the cell below the mounted membrane is completely filled with receptor fluid (0.1M sodium acetate buffer, pH 4.0) such that the receptor fluid is in contact with the skin. The receptor fluid is stirred by means of a magnetic stir bar 27 and a magnetic stirrer (not illustrated). The sampling port 29 is covered except when in use.

When a gel formulation is evaluated, the skin is placed across the opening of the lower portion of the diffusion cell. A 300 mg portion of formulation is spread evenly over the skin. The diffusion cell is assembled and the lower portion is filled with 10 mL of warm (32±1° C.) receptor fluid.

The sampling port is covered and the cell is placed in a constant temperature (32±1° C.) and humidity (45%±15% relative humidity) chamber. The receptor fluid is stirred throughout the experiment. The entire volume of receptor fluid is withdrawn at intervals of 3, 6, 12, 24, 48 and 72 hours elapsed time and immediately replaced with fresh fluid. The first 5 mL of withdrawn fluid is filtered through a 0.45μ Acrodisc CRPTFE 25 mm filter (Miltex Instument Company, Ohio) and discarded. Then a 1mL portion is filtered and placed in a high performance liquid chromatography vial. The vial is capped then refrigerated until analysis. The sample is analyzed for 4-amino-2-ethoxymethyl-α,α-dimethyl-1H-imidazo[4,5-c]quinoline-1-ethanol using high performance liquid chromatography (Column: 15 cm×0.46 cm Supelcosil LC-8-DB (Supelco, Inc., Bellefonte, Pa., USA), 5 μm particle size; Mobile phase: acetonitrile/75 mM ammonium phosphate aqueous buffer with 5 mM triethyl amine, pH 2.5, 19%/81% v/v; Flow rate: 2.0 L/min; Detector: uv at 245 nm). Results are reported as the cumulative amount of drug penetrating at 3, 6, 12, 24, 48 and 72 hours and are expressed in units of μg/mL.

EXAMPLE 1

4-Amino-2-ethoxymethyl-α,α-dimethyl-1H-imidazo[4,5-c]quinoline-1-ethanol (0.75 g) was added to triacetin (272.25 g) in a 600 mL glass beaker. The resulting mixture was heated (about 55° C.) with stirring until all of the drug was dissolved. Colloidal silicon dioxide (27.0 g, AEROSIL® 200 from Degussa, Frankfurt, Germany) was added to the solution and mixed with a spatula until wetted. The mixture was sheared on a high speed propeller mixer until a homogeneous gel was formed. The gel contained 0.25% 4-amino-2-ethoxymethyl-α,α-dimethyl-1H-imidazo[4,5-c] quinoline-1-ethanol, 9.0% colloidal silicon dioxide, and 90.75% triacetin.

EXAMPLE 2

Propylene glycol (20.0 g), triacetin (343.0 g) and 4-amino-2-ethoxymethyl-α,α-dimethyl-1H-imidazo[4,5-c] quinoline-1-ethanol ( 1.0 g) were placed in a 600 mL glass beaker then heated (50°±5° C.) with stirring until all of the drug was dissolved. Colloidal silicon dioxide (36.0 g) was added to the solution and mixed with a spatula until wetted. The mixture was sheared on a high speed propeller mixer until a homogeneous gel was formed. The gel contained 0.25% 4-amino-2-ethoxymethyl-α,α-dimethyl-1H-imidazo [4,5-c]quinoline-1-ethanol, 5.0% propylene glycol, 9.0% colloidal silicon dioxide, and 85.75% triacetin.

EXAMPLE 3

Propylene glycol (80.0 g) and 4-amino-2-ethoxymethyl-α,α-dimethyl-1H-imidazo[4,5-c]quinoline-1-ethanol (1.0 g) were placed in a 600 mL glass beaker then heated (about 50° C.) with stirring until all of the drug was dissolved. Triacetin (283.0 g) was added and the resulting mixture was stirred until a solution was obtained. The heat was turned off. Colloidal silicon dioxide (36.0 g) was added to the solution and mixed with a spatula until wetted. The mixture was sheared on a high speed propeller mixer until a homogeneous gel was formed. The gel contained 0.25% 4-amino-2-ethoxymethyl-α,α-dimethyl-1H-imidazo[4,5-c]quinoline-1-ethanol, 20.0% propylene glycol, 9.0% colloidal silicon dioxide, and 70.75% triacetin.

The gel formulations of Examples 1–3 were tested for their ability to induce cytokines using the test method described above. The results shown in Table 1 below demonstrate that all three formulations produced significant interferon and tumor necrosis factor induction at the site of 4-amino-2-ethoxymethyl-α,α-dimethyl-1H-imidazo[4,5-c] quinoline-1-ethanol application. Results are presented as the mean±standard error mean of 4 animals assayed individually. ND means not done.

TABLE 1

| | | Cytokine Induction | | | |
| | | Cytokine Concentration | | | |
| | | Right Flank | | Left Flank | |
| Formulation | Time (hr) | IFN (U/mL) | TNF (pg/mL) | IFN (U/mL) | TNF (pg/mL) |
|---|---|---|---|---|---|
| 1 | 1 | 346 ± 54 | 699 ± 187 | 86 ± 37 | 273 ± 65 |
| 1 | 2 | 215 ± 107 | 496 ± 123 | 106 ± 98 | 344 ± 95 |
| 2 | 1 | 277 ± 80 | 340 ± 97 | 127 ± 71 | 163 ± 24 |
| 2 | 2 | 210 ± 70 | 610 ± 83 | 106 ± 105 | 237 ± 42 |
| 3 | 1 | <1 ± 0 | 304 ± 39 | <1 ± 0 | 165 ± 20 |

TABLE 1-continued

Cytokine Induction

| Formulation | Time (hr) | Right Flank IFN (U/mL) | Right Flank TNF (pg/mL) | Left Flank IFN (U/mL) | Left Flank TNF (pg/mL) |
|---|---|---|---|---|---|
| 3 | 2 | 577 ± 210 | 1138 ± 232 | 105 ± 98 | 454 ± 175 |
| Untreated | 0 | 3± 1 | 120 ± 15 | ND | ND |

EXAMPLE 4

Using the method of Example 1, a gel containing 0.05% 4-amino-2-ethoxymethyl-α,α-dimethyl-1H-imidazo[4,5-c]quinoline-1-ethanol, 9.0% colloidal silicon dioxide, and 90.95% triacetin was prepared.

EXAMPLE 5

Using the method of Example 2, a gel containing 0.05% 4-amino-2-ethoxymethyl-α,α-dimethyl-1H-imidazo[4,5-c]quinoline-1-ethanol, 5.0% propylene glycol, 9.0% colloidal silicon dioxide, and 85.95% triacetin was prepared.

EXAMPLE 6

Using the method of Example 3, a gel containing 0.05% 4-amino-2-ethoxymethyl-α,α-dimethyl-1H-imidazo [4,5-c]quinoline-1-ethanol, 20.0% propylene glycol, 9.0% colloidal silicon dioxide, and 70.95% triacetin was prepared.

The gel formulations of Examples 4–6 were tested for their ability to induce cytokines using the test method described above. The results shown in Table 2 below demonstrate that all three formulations produced significant interferon and tumor necrosis factor induction at the site of 4-amino-2-ethoxymethyl-α,αdimethyl-1H-imidazo[4,5-c]quinoline-1-ethanol application. Results are presented as the mean±standard error mean of 4 animals assayed individually. ND means not done.

TABLE 2

Cytokine Induction

| Formulation | Time (hr) | Right Flank IFN (U/mL) | Right Flank TNF (pg/mL) | Left Flank IFN (U/mL) | Left Flank TNF (pg/mL) |
|---|---|---|---|---|---|
| 4 | 1 | 0.9 ± 0.5 | 412 ± 105 | <1.0 | 280 ± 51 |
| 4 | 2 | 20 ± 10 | 345 ± 72 | <1.0 | 153 ± 19 |
| 5 | 1 | 0.3 ± 0.3 | 348 ± 35 | <1.0 | 262 ± 26 |
| 5 | 2 | 69 ± 58 | 346 ± 24 | <1.0 | 194 ± 19 |
| 6 | 1 | <1 ± 0 | 279 ± 45 | <1.0 | 170 ± 40 |
| 6 | 2 | 43 ± 32 | 260 ± 47 | <1.0 | 129 ± 41 |
| Untreated | 0 | <1.0 | 220 ± 28 | ND | ND |

EXAMPLE 7

Using the method of Example 1, a gel containing 0.01% 4-amino-2-ethoxymethyl-α,α-dimethyl-1H-imidazo[4,5-c]quinoline-1-ethanol, 9.0% colloidal silicon dioxide, and 90.99% triacetin was prepared.

EXAMPLE 8

Using the method of Example 2, a gel containing 0.01% 4-amino-2-ethoxymethyl-α,α-dimethyl-1H-imidazo[4,5-c]quinoline-1-ethanol, 5.0% propylene glycol, 9.0% colloidal silicon dioxide, and 85.99% triacetin was prepared.

EXAMPLE 9

Using the method of Example 3, a gel containing 0.01% 4-amino-2-ethoxymethyl-α,α-dimethyl-1H-imidazo[4,5-c]quinoline-1-ethanol, 20.0% propylene glycol, 9.0% colloidal silicon dioxide, and 70.99% triacetin was prepared.

The gel formulations of Examples 7–9 were tested for their ability to induce cytokines using the test method described above. The results shown in Table 3 below monstrate that the formulation of Example 8 produced significant tumor necrosis factor induction at the site of 4-amino-2-ethoxymethyl-α,α-dimethyl-1H-imidazo[4,5-c]quinoline-1-ethanol application. Results are presented as the mean±standard error mean of 4 animals assayed individually. ND means not done.

TABLE 3

Cytokine Induction

| Formulation | Time (hr) | Right Flank IFN (U/mL) | Right Flank TNF (pg/mL) | Left Flank IFN (U/mL) | Left Flank TNF (pg/mL) |
|---|---|---|---|---|---|
| 7 | 1 | <1.0 | 455 ± 93 | <1.0 | 421 ± 63 |
| 7 | 2 | <1.0 | 382 ± 86 | <1.0 | 398 ± 54 |
| 8 | 1 | <1.0 | 406 ± 25 | <1.0 | 316 ± 31 |
| 8 | 2 | <1.0 | 296 ± 23 | <1.0 | 375 ± 18 |
| 9 | 1 | <1.0 | 380 ± 43 | <1.0 | 352 ± 52 |
| 9 | 2 | <1.0 | 296 ± 23 | <1.0 | 366 ± 56 |
| Untreated | 0 | <1.0 | 273 ± 44 | ND | ND |

EXAMPLE 10

Using the method of Example 3, a gel containing 0.25% 4-amino-2-ethoxymethyl-α,α-dimethyl-1H-imidazo[4,5-c]quinoline-1-ethanol, 20.0% propylene glycol, 8.0% colloidal silicon dioxide, and 71.75% triacetin was prepared.

EXAMPLE 11

Using the method of Example 3, a gel containing 0.25% 4-amino-2-ethoxymethyl-α,α-dimethyl-1H-imidazo[4,5-c]quinoline-1-ethanol, 20.0% propylene glycol, 10.0% colloidal silicon dioxide, and 69.75% triacetin was prepared.

The gel formulations of Examples 2, 3, 5, 6, 8, 10 and 11 were tested for their ability to release 4-amino-2-ethoxymethyl-α,α-dimethyl-1H-imidazo[4,5-c]quinoline-1-ethanol using the test method described above. The results shown in Table 4 below demonstrate that all five formulations release 4-amino-2-ethoxymethyl-α,α-dimethyl-1H-imidazo[4,5-c]quinoline-1-ethanol. Each value is the mean of the values from 6 diffusion cells.

TABLE 4

Drug Release

Cumulative Amount Released (mg/cm$^2$)

| Formulation | 30 min | 60 min | 120 min | 240 min | 360 min |
|---|---|---|---|---|---|
| Example 2 | 0.13 | 0.18 | 0.24 | 0.41 | 0.56 |
| Example 3 | 0.15 | 0.23 | 0.33 | 0.50 | 0.62 |
| Example 5 | 0.03 | 0.04 | 0.05 | 0.09 | 0.11 |

TABLE 4-continued

Drug Release

Cumulative Amount Released (mg/cm$^2$)

| Formulation | 30 min | 60 min | 120 min | 240 min | 360 min |
|---|---|---|---|---|---|
| Example 6 | 0.03 | 0.04 | 0.07 | 0.12 | 0.15 |
| Example 8 | 0.024 | 0.041 | 0.062 | 0.091 | 0.108 |
| Example 10 | 0.14 | 0.22 | 0.33 | 0.58 | 0.72 |
| Example 11 | 0.12 | 0.17 | 0.25 | 0.45 | 0.59 |

The in vitro penetration of 4-amino-2-ethoxymethyl-α,α-dimethyl-1H-imidazo[4,5-c]quinoline-1-ethanol through hairless mouse skin or human cadaver skin from a gel formulation of Example 3 was determined using the test method described above. The results shown in Table 5 below demonstrate that the gel releases 4-amino-2-ethoxymethyl-α,α-dimethyl-1H-imidazo[4,5-c]quinoline-1-ethanol to and through the skin. Each value shown is the average of six independent determinations with the standard deviation.

TABLE 5

In Vitro Skin Penetration

Cumulative Amount Penetrating (μg/mL)

| Time (hours) | Hairless Mouse Skin | Human Cadaver Skin |
|---|---|---|
| 3 | 0.073 ± 0.08 | 0 |
| 6 | 0.147 ± 0.133 | 0 |
| 12 | 0.413 ± 0.210 | 0 |
| 24 | 1.085 ± 0.380 | 0 |
| 48 | 2.89 ± 1.18 | 0.292 ± 0.088 |
| 72 | 5.455 ± 3.88 | 0.493 ± 0.158 |

What is claimed is:

1. A method of inducing the production of cytokines locally in the skin or mucous membranes of a mammal, comprising placing on the skin or mucous membranes of a mammal an amount of a gel formulation comprising:

(a) 4-amino-2-ethoxymethyl-α,α-dimethyl-1H-imidazo[4,5-c]quinoline-1-ethanol in an amount effective to induce cytokines;

(b) colloidal silicon dioxide and (c) triacetin.

2. The method of claim 1, where the gel formulation is applied to lesions on the skin and/or mucosa.

3. The method of claim 1 wherein the gel formulation further comprises propylene glycol.

4. A method of inducing the production of interferon locally in the skin or mucous membranes of a mammal, comprising placing on the skin or mucous membranes of a mammal an amount of a gel formulation comprising:

(a) 4-amino-2-ethoxymethyl-α,α-dimethyl-1H-imidazo[4,5-c]quinoline-1-ethanol in an amount effective to induce cytokines;

(b) colloidal silicon dioxide and (c) triacetin.

5. The method of claim 4 wherein the gel formulation further comprises propylene glycol.

6. A method of inducing the production of tumor necrosis factor locally in the skin or mucous membranes of a mammal, comprising placing on the skin or mucous membranes of a mammal an amount of a gel formulation comprising:

(a) 4-amino-2-ethoxymethyl-α,α-dimethyl-1H-imidazo[4,5-c]quinoline-1-ethanol in an amount effective to induce cytokines;

(b) colloidal silicon dioxide and (c) triacetin.

7. The method of claim 6 wherein the gel formulation further comprises propylene glycol.

* * * * *